United States Patent [19]

Watson

[11] 4,158,906
[45] Jun. 26, 1979

[54] DIAPER CINCH

[76] Inventor: Sheldon Watson, 1300 Adams No. 10-A, Costa Mesa, Calif. 92926

[21] Appl. No.: 872,680

[22] Filed: Jan. 26, 1978

[51] Int. Cl.² .............................................. A44B 21/00
[52] U.S. Cl. ..................................... 24/83; 24/81 AA; 24/81 AG; 24/252 R; 24/204
[58] Field of Search .................. 24/81 AS, 83, 85 A, 24/86 A, 88, 84 A, 81 GS, 81 R, 81 SK, 81 T, 81 TC, 82, 87 R, 73 A, 73 M, 73 C, 73 LA, 252, 253; 2/DIG. 6, 325, 323, 335, 309; 128/DIG. 15

[56] References Cited

U.S. PATENT DOCUMENTS

| 202,735 | 4/1878 | Lindsay | 24/81 AL |
|---|---|---|---|
| 211,479 | 1/1879 | Shelby | 24/81 AG |
| 343,715 | 6/1886 | Lind | 24/73 MC |
| 552,198 | 12/1895 | Porter | 24/81 GS |
| 665,479 | 1/1901 | Smith | 24/87 R |
| 1,499,592 | 7/1924 | Phillips | 24/253 |
| 1,616,267 | 2/1927 | Laird | 2/323 |
| 1,896,029 | 1/1933 | Gunther | 24/253 |
| 1,900,613 | 3/1933 | Parker | 24/253 |
| 2,654,132 | 10/1953 | Norcross | 24/81 GS |
| 2,927,583 | 3/1960 | Powell | 24/87 R |
| 2,962,784 | 12/1960 | Gianios | 24/88 |
| 3,057,354 | 10/1962 | Roberts | 24/204 |
| 3,259,916 | 7/1966 | Stepniak | 2/323 |
| 3,374,508 | 3/1968 | Slinovitz | 24/204 |
| 3,727,272 | 4/1973 | Rhodes | 24/81 AB |
| 3,893,725 | 7/1975 | Coulter | 24/81 AG |

FOREIGN PATENT DOCUMENTS 570419 7/1945 United Kingdom ...................... 24/253

Primary Examiner—Bernard A. Gelak
Attorney, Agent, or Firm—Fulwider, Patton, Rieber, Lee & Utecht

[57] ABSTRACT

A diaper cinch is formed of a pair of independent jaws from each of which trails a strap having a velcro pad thereon. The jaws grasp edges of the diaper inserted therein in releasable fashion on either side of the torso of the baby. The straps are then arranged to extend toward each other and in juxtaposition with the velcro pads placed against each other to cinch the diaper about the girth of the baby.

11 Claims, 6 Drawing Figures

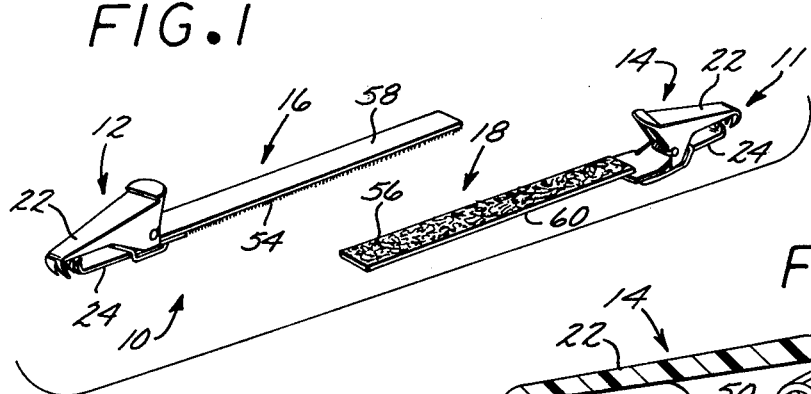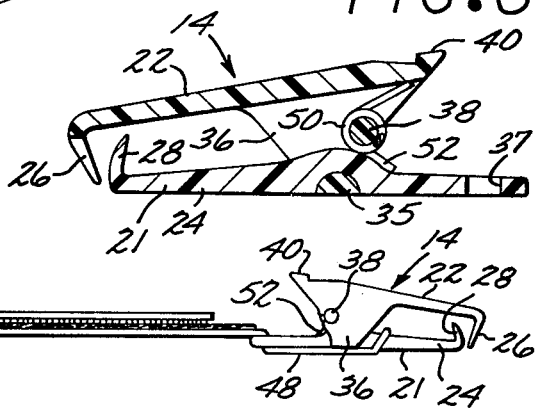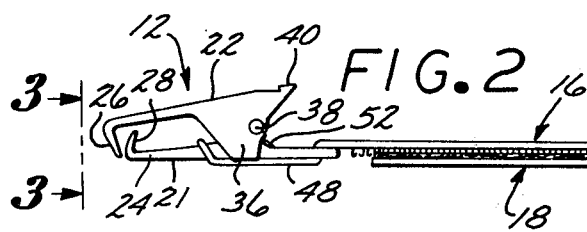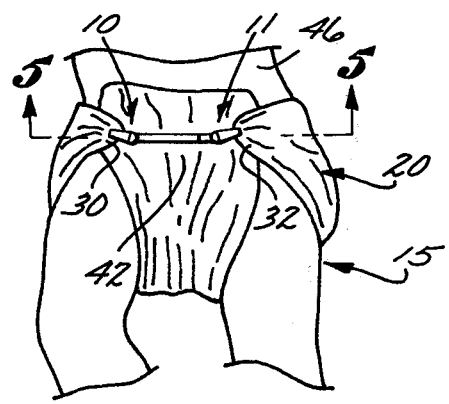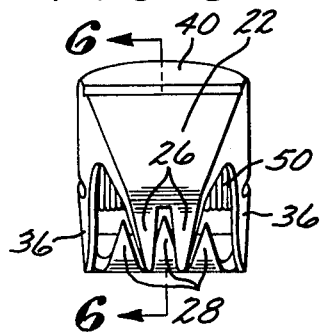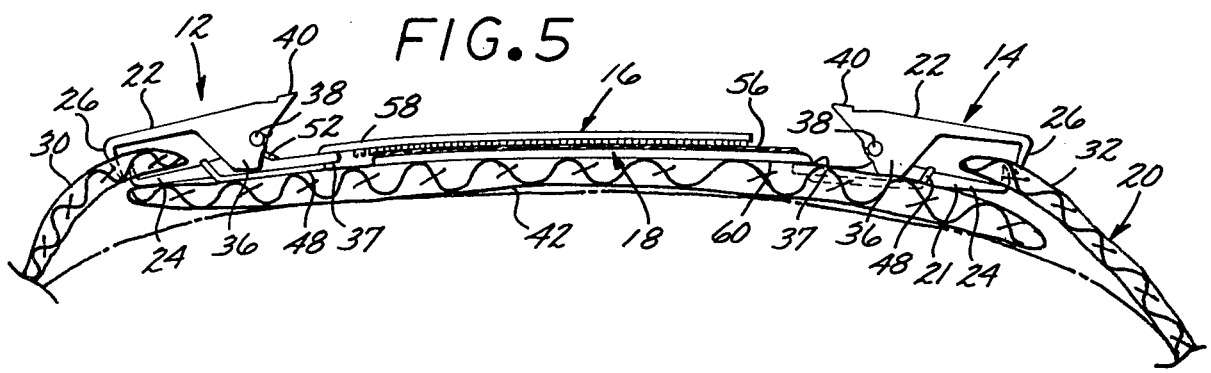

DIAPER CINCH

BACKGROUND OF THE INVENTION

1. Field of the Invention

The present invention relates to reuseable devices for fastening diapers upon the torso of an infant human being.

2. Description of the Prior Art

For many years the standard and unquestioned means of fastening cloth diapers to the torso of an infant has been by use of large safety pins. To fasten a diaper using safety pins, an infant is laid on its back upon the diaper with the diaper extending downward from the baby's waist. The free end of the diaper is then brought upward and forward to encompass the baby's crotch area and the edges of the front portion of the diaper are brought rearward and disposed in layered arrangement adjacent to the edges of the rear portion of the diaper at the baby's side. The pointed spear of the safety pin is then passed through the layers of diapers, penetrating the innermost layer both entering and reentering. The exposed point of the safety pin spear then becomes accessible for capture by the safety pin guard. The safety pin guard holds the pin shut, thus securing the diaper into place on one side of the baby. A second safety pin is used in similar fashion to fasten the edges of the diaper together at the infant's other side.

While having remained the accepted means of fastening cloth diapers together for many years, the enlarged reusable safety pins as described have presented numerous problems. It is quite difficult to pinch the double layers of diaper fabric together at the baby's sides to form a fold of at least four layers in thickness, and then penetrate all four layers with the spear of the safety pin. The strength required is beyond that which can be exercised with facility by most adults, with the consequence that the baby is frequently jarred and jostled during a diaper change. Moreover, because of the strength required, the layers of fabric typically require a backing against which the spear of the safety pin is directed. This backing normally is provided by the only convenient means available, which are the digits or fingers of the adult performing the diaper change. Ideally the spear of the safety pin emerges between adjacent fingers of the hand of the adult providing the backing, or adjacent to one of the fingers. However, and much to the pain and chagrin of the adult performing the diaper change, the spear frequently is misdirected and penetrates the skin of the adult performing the diaper change.

A futher hazard in fastening the edges of diapers together using safety pins is the danger to the infant itself. Frequently, upon entering the inner most fabric layer adjacent the baby's skin, the spear of the safety pin is inadvertently directed toward the baby's skin and pricks the skin causing the baby anguish and bringing an immediate reaction of outrage. Moreover, even if a diaper change is successfully effectuated, the baby is still sometimes frequently stuck with a diaper pin when the tip of the spear of the safety pin inadvertently becomes disenaged from the safety pin guard. This is an especially frequent occurrence with infants who are quite active. The result is that at least some of the layers of the diaper pull free from the spear of the safety pin, and continued movement of the infant results in the spear of the safety pin pricking the baby's skin.

Various alternative techniques of fastening diapers using conventional oversized safety pins have been attempted, but all with unsatisfactory results. For example, instead of drawing the edges of the diaper together in overlapping fashion with the inside surface of one edge in contact with the outer surface of another diaper edge, the edges of the diapers have sometimes been drawn together in pinched fashion with the inner surface of one edge facing the inner surface of the opposing edge. This is done to reduce the number of thicknesses of fabric through which the spear of the safety pin must pass. The difficulty, however, is that when released, the edges of the diaper which are to be fastened together are drawn apart a short distance as determined by the length of the safety pin. One of the diaper edges is restrained by the safety pin guard while the other is restrained by the fulcrum for the safety pin spear. The length of the safety pin bridges the gap therebetween, but the separation is sufficient so that the body wastes of the infant frequently escape the confines of the diaper. This generates a considerable cleaning chore for the parent or other guardian of the infant. Moreover, the shank of the safety pin spear and spine ride in contact with the baby's skin, and thus provide a source of irritation to the baby.

Numerous other types of fasteners have been attempted for use in securing the edges of diapers together, but all such devices have heretofore proven too cumbersome for the ease of manipulation required in performing a diaper change. Hence, all have been discarded as not warranting the effort required for their use.

With the advent of paper diapers, other forms of fasteners gained some degree of use. Specifically, the external plasticized surface provided with most paper disposable diapers provided a surface to which a pressure sensitive adhesive coated tape would adhere with some degree of success. The same was not true when such tape is applied to reusable cloth diapers, however. Nevertheless such adhesive tape still tends somewhat to disengage from the plasticized outer surface of disposable diapers, and in any event is entirely unsuitable for use with reuseable cloth diapers.

SUMMARY OF THE INVENTION

It is an object of the present invention to provide a reusable means for fastening diapers upon the torso of a child which requires a minimum of manual manipulation. This is achieved by the use of a pair of jaws, each of which includes a pair of spring biased mandibles that are forced together and grasp the edge of a diaper inserted therebetween.

A further object of the invention is to provide diaper fasteners which can be manipulated to a great degree prior to pulling the edges of the diaper into position for fastening about the torso of a baby. Because the diaper cinch of the present invention is divided into two separate portions, the jaw member associated with each portion can be clamped onto the edge of a diaper even before the child is laid upon the diaper. Once the jaws are in place, the baby is laid upon the diaper, the diaper is drawn about the baby and the straps trailing from each of the jaws are brought into juxtaposition to draw the diaper snugly about the baby's torso. The straps are then pressed together and the pressure sensitive pads, typically velcro pads, adhere to each other and hold the diaper cinch firmly in position until the next diaper change.

Yet a further object of the invention is to provide diaper fasteners which cannot inadvertently be loosened and present a safety hazard to the diapered infant. The mandibles of each of the jaws are hinged about an axle located well to the rear of a set of teeth on each mandible. The lever arm behind the axle on at least one of the mandibles is relatively short, so that a fair degree of pressure is required to open the jaws. This prevents an infant from inadvertently using his fingers to open the jaws, thus loosening the diaper. Furthermore, even if the infant rolls over or presses the jaws against a rigid object, such as the rails of a crib or play pen, the lever arm of the mandible is still too short for the jaw to be opened. However, the lever arm with which the mandibles are opened by an adult performing a diaper change is sufficiently long so that an adult of normal strength can use opposing digits of his or her hand to overcome the spring bias of the mandibles to spread the teeth of the jaws apart to release the edge of a soiled diaper and to insert the edge of a fresh diaper therebetween.

Still an additional object of the invention is to provide a means for fastening diapers which does not present the hazard of causing a puncture wound to either the child upon whom diapers are fastened or the adult effectuating a diaper change. Unlike conventional safety pins, the diaper cinch of the present invention requires no penetration of the layers of diaper fabric by a pointed shaft, such as the spear of a safety pin, or by any object similar thereto. Rather, the mandibles of each of the jaws clamp against each other and require no additional backing in order to be properly positioned in place. Furthermore, no penetration of the fabric is necessary. This not only presents less of a hazard to the individuals involved, but also tends to preserve the structure of the diaper itself, since tearing of the fabric is unlikely to be initiated without penetration.

Still a further object of the invention is to provide a diaper cinch which will accomodate different waistlines. As the baby grows, or perhaps as different thickness or types of diapers are required for night changes and for daytime changes, the diaper cinch of the present invention is easily adjusted accordingly. Because the opposing diaper cinch straps are releasably positioned relative to each other with each diaper change, any change of girth is easily accommodated. This allows a baby to swathed in two diapers at night, when the greatest weight of body wastes are to be received, yet requires no adjustment for wrapping the child in a single diaper during the daytime.

The present invention may be explained with greater particularity and clarity by reference to the accompanying drawing figures.

DESCRIPTION OF THE DRAWINGS

FIG. 1 is a perspective view of the separated elements of the diaper cinch of the invention.

FIG. 2 is a side elevational view of the elements of the diaper cinch fastened together.

FIG. 3 is an end view of one of the jaws of the diaper cinch taken along the lines of 3—3 of FIG. 2.

FIG. 4 illustrates the positioning of a diaper about the torso of a baby using the diaper cinch of the present invention.

FIG. 5 illustrates diagrammatically the manner of attachment of a diaper using the diaper cinch, taken along the lines 5—5 of FIG. 4.

FIG. 6 is a sectional view of a jaw taken along the lines 6—6 of FIG. 3.

DESCRIPTION OF THE EMBODIMENT

With reference to FIG. 1 it can be seen that the diaper cinch of the invention includes a pair of separate independent elements 10 and 11, each of which includes an independent jaw member 12 or 14 biased toward a locked disposition, and a reusable trailing pressure sensitive immobilizing strap 16 or 18. The straps 16 and 18 are used to fasten the independent elements 10 and 11 of the diaper cinch together and are arranged for mutual releasable interaction to secure a diaper 20, indicated in FIGS. 4 and 5, about the girth of an infant 15.

Each of the jaws 12 and 14 is formed of a hard plastic or alternatively some water resistant metal, such as stainless steel or aluminum, and includes a pair of opposing mandibles 22 and 24. Each mandible is shaped with an elongated flat spine terminating at one end in teeth 26 or 28. The teeth 26 and 28 are arranged at acute angles with respect to the elongated mandible spines of the mandibles 22 and 24. The exposed teeth 26 of the outer or exposed mandibles 22 overhang and cover the teeth 28 of the innermost mandibles 24 in an overbite, as indicated most explicitly in FIGS. 2 and 5. The teeth 28 of the underbiting mandibles form an acute angle relative to the spines of the mandibles 24, less than the acute angle that the teeth 26 form relative to the outer mandible 22, as illustrated in FIG. 2. This arrangement aids in locking the edges 30 and 32 of the diaper 20 and preventing these edges from slipping outwardly from the jaws 12 and 14 when the diaper is subjected to circumferential stress, as depicted in FIG. 5.

Opposite the teeth 26, the spines of the mandibles 22 extend in relative elongation and ultimately spread to form inwardly turned ears 36 which are notched with concave recesses that capture a cylindrical rod 38 extending perpendicular to the ears 36. As illustrated in FIG. 6, the ears 36 extend down below the underside of the mandible 24 and are joined together at their lower extremities by a transverse bar 35, which captures the mandible 24 within a transverse seat of semicircular cross section in the mandible 22. The mandibles 22 and 24 are thereby mounted in hinged disposition and rotate relative to each other about the bottom of the bar 35. A coil spring 50 is positioned concentrically about the rod 38, and has ends 51 and 52, which extend rearward to bias the mandibles 22 and 24 so that the teeth 26 and 28 thereof are forced together. At the rearward extremity of the spines of the mandible 22 and ears 36, a transverse pressure plate 40 is provided extending parallel to the rod 38. The pressure plate 40 is located slightly to the rear of the rod 38, so that pressure applied thereto by the fingers of an individual changing diapers on the baby 15 is applied through a short lever arm, relative to the rod 38.

It can be seen that as pressure is applied to the pressure plate and to the underside of the mandible 24, to the rear of the bar 35, that the entire upper portion of the mandible 22, including the rod 38 and spring 50, are rotated rearwardly relative to the bar 35. By moving in relative rotation about the bar 35, rather than about an intermediate axle, such as in the approximate position of the rod 38, the separation between the teeth 26 and 28 is markedly increased when the jaws are opened, thereby increasing the thicknesses of materials and objects which can be inserted therebetween.

The opposing or innermost of the mandibles 24 of each of the jaws 12 and 14 includes a spine having a flattened backside 21 extending from the teeth 28 rearward past the rearmost limit of the pressure plate 40 of the opposing mandible 22. The flattened backside 21 of the mandibles 24 bears against the front flap 42 of the fabric of the diaper 20 to exert a generally uniform pressure thereon which is transmitted likewise uniformly to the torso 46 of the infant 15, as illustrated in FIG. 5. Within the flattened backsides 21 of the mandibles 24, remote from the teeth 28 thereof, openings are defined to receive the extremity 48 of the fastening strap 16 or 18. For attachment to the jaws 12 and 14, the extremity 48 of each of the straps 16 and 18 is passed through the opening 37 in the flattened backside 21 of the mandible 24 and forward therefrom. The extremities 48 of the straps 16 and 18 themselves are defined with an aperture therein. The extremities 48 of the straps 16 and 18 are then looped over the teeth 28 of the mandibles 24 and impaled thereon. When tensile force draws upon the straps 16 and 18, the extremities 48 thereof are pulled snugly about the rearward portion of the spines of the mandibles 24 and seat themselves in the general proximity of the rods 38. Thus, the straps 16 and 18 are securely fastened to the jaws 12 and 14 during use, but can be drawn forward and withdrawn from the teeth 28 for replacement if they should become worn or ineffective.

The mandibles 22 and 24 are biased together so that the teeth 26 and 28 tend to clamp and grasp an edge 30 or 32 of the diaper 20. Biasing in this regard is achieved by means of a coil spring 50 positioned upon the axles 38 between the confines of opposing ears 36 of the mandibles 22. The coil springs 50 each terminate in radially extending wire arms, such as the arms 52 visible in FIGS. 2 and 5. The arms 52 bear against the structure of the mandibles 22 and 24 to bias the teeth 26 and 28 toward each other in locked arrangement. By means of the springs 50, the mandibles 22 and 24 of each of the jaws 12 and 14 are biased in opposition towards locked disposition to grasp and immobilize a portion of the diaper 20, such as the edges 30 and 32 of the diaper 20, visible in FIG. 5.

The bias of the mandibles 22 and 24 may be overcome by exerting pressure using the opposing fingers of one hand upon the pressure plate 40 of the mandible 22 and upon the flattened backside 21 of the mandible 24 in the vicinity of the aperture 37 therein. The mandibles 22 and 24 of each jaw 12 and 14 are thereby coupled to each other and disposed to move in relative rotation about the rods 38.

The trailing extremities of each of the straps 16 and 18 includes some form of pressure sensitive immobilizing structure, such as the velcro pads 54 and 56 depicted in FIGS. 1, 2 and 5. The velcro pads 54 and 56 are respectively fastened to pliant fabric straps 58 and 60 respectively by means of glue or some other form of permanent waterproof adhesive. As with conventional velcro pads, one of the pads, the pad 54, for example, has an exposed fastening surface from which a multiplicity of yieldable hooks are directed outward. The opposing pad 56 on the strap 18 includes a contact pad secured to the pliant strap 60 and having an exposed fastening surface from which a looped pile is directed outward. The contact pads 54 are thereby positionable with their fastening surfaces in face to face relationship with the fastening surfaces of contact pads 56. The hooks in the pad 54 are thereby engageable with the pile of the pad 56 to longitudinally immobilize the straps 16 and 18 relative to each other, despite tensile forces between the jaws 12 and 14 tending to pull the jaws 12 and 14 apart.

Such forces typically develop as a result of twisting and agitation of the torso of the baby 15. This occurs as a result of the natural body movements of the baby.

To use the diaper cinch of the invention the jaws 12 and 14, with straps 16 and 18 separated so that the structure is divided into its two separate elements 10 and 11, are clamped to the edges 30 and 32 of a diaper 20, as depicted in FIG. 5. Clamping is achieved by opening the jaws 12 and 14 to receive the edges 30 and 32. The jaws are opened by squeezing the pressure plate 40 and flattened backside 21 of the mandibles 24 adjacent the openings 37 therein. This forces the teeth 26 and 28 apart and allows the edges 30 and 32 of the diaper 20 to be inserted therebetween. When the pressure plates 40 and flattened backsides 21 of the mandibles 24 are released, the springs 50 force the mandibles 22 and 24 shut, thus locking the edges 30 and 32 of the diaper 20 between oppoisng sets of the overbitting exposed teeth 26 and the underbiting covered teeth 28.

Attachment of the jaws 12 and 14 to the edges 30 and 32 of the diaper can be performed before the diaper is even brought into the vicinity of the baby 15. This faciliates attachment considerably. Once the jaws 12 and 14 are secured into position on the edges 30 and 32 of a pair of adjacent corners of the diaper 20, the baby 15 is laid supine upon the diaper 20 with the edges 30 and 32 near the baby's waist. The edges 30 and 32 are brought forward and the front flap 42 is drawn forward and upward to cover the crotch area of the baby. The corners 30 and 32 of the diaper 20 are drawn forward along the baby's sides and the straps 16 and 18 trailing from the jaws 12 and 14 and drawn snugly into juxtaposition relative to each other. The contact patches 54 and 56 on the straps 16 and 18 are then forced together, so that the opposing velcro surfaces engage each other. This draws the corners 30 and 32 snugly about the hips of the baby 10 while the diaper cinch of the invention, once more connected in a unified structure, overwraps the flap 42 of the diaper 20 and secures the diaper into position on the torso 46 of the baby 10. The upper extremity of the flap 42 can then be folded down and over the strap member 16 and 18 of the diaper cinch.

To change diapers, the velcro pads 54 and 56 are merely peeled from each other, thus freeing the flap 42 of the diaper 20. The diaper can then be removed and the jaws 12 and 14 detached from the soiled diaper. The jaws 12 and 14 are then attached to corresponding corners 30 and 32 of a fresh diaper 20, and fastened about the torso 46 of the infant 15 in the manner previously described. The jaws 12 and 14 may also be additionally fastened to the edges of the flap 42, to prevent the flap 42 from being drawn down below the diaper cinch. This fastening arrangement is particularly useful with infants once they begin to crawl and walk.

Both of the mandibles 22 and 24 of the jaws 12 and 14, as well as rods 38 thereof, are preferably formed of molded plastic, such as polyvinylchloride or nylon. The springs 50 are normally, steel, but should be coated with a moisture resistant coating. The straps 58 and 60 are preferably formed of a pliant but inelastic material such as nylon or plastic. The velcro pads 54 and 56 are also formed of plastic.

While but a single embodiment of the invention has been depicted herein, it must be understood that numerous variations and modifications will become readily apparent to those familiar with diaper fastening techniques without departing from the concept and scope of the invention, which is defined in the claims appended hereto.

I claim:

1. A diaper cinch comprising a pair of independent jaws biased toward a locked disposition wherein each of said jaws is formed by a pair of opposing mandibles each having a leading end with teeth and a trailing end remote therefrom, one mandible being longer and one shorter than the other, the shorter mandible of each jaw having a pair of ears with a transverse bar connected therebetween, and said mandibles are disposed to effectuate relative rotation about said bar which serves as an axle located in a seat at the backside of the longer one of said mandibles remote from said shorter mandible, and said shorter mandible terminates a short distance beyond said axle remote from the end with teeth to provide a very short moment arm at its trailing end for forces acting thereon to compress said trailing ends of said longer and shorter mandibles together to effectuate relative rotation about said axle, spring biasing means secured relative to said ears of shorter mandible between said mandibles and between said axle and said short moment arm of said shorter mandible and acting upon said longer mandible to bias said trailing ends of said longer and shorter mandibles apart and to hold said axle in said seat at said backside of said longer mandible, and flexible reusable trailing pressure sensitive strips each having a plurality of interlocking means extending from both of said longer mandibles of each of said jaws for mutual releasable interaction to secure a diaper about the girth of a child.

2. The diaper cinch according to claim 1 further characterized in that each of said interlocking means is comprised of a velcro pad affixed to a strap trailing from each of said pair of jaws.

3. The diaper cinch according to claim 1 further characterized in that at least one of said mandibles of each of said jaws has a flattened backside adapted to bear against the torso of an individual with a uniform pressure thereacross.

4. A diaper cinch according to claim 1 further characterized in that in said jaws the teeth of one of said mandibles overbite the teeth of the other to grasp an edge of a diaper, each jaw requiring the strength of opposing digits of the hand of an adult human being to overcome said spring bias to draw said teeth apart to release said diaper.

5. The diaper cinch according to claim 1 further characterized in that said longer mandible of each of said jaws in which said bar is seated encloses a smaller cross sectional area at a location at said teeth than at a location proximate to said bar and has an opening in the trailing end therein, and one of said pressure sensitive strips trails therefrom and has an extremity with an aperture therein of a cross sectional area greater than the cross sectional area of said mandible from which it trails at said location at said teeth and less than the cross sectional area of said mandible at said location proximate to said bar, whereby said extremity of said pressure sensitive strip is looped over the teeth of said mandible and drawn snugly rearward through said opening in said mandible in said trailing end.

6. A diaper cinch comprising a pair of jaws biased to close about edges of a diaper inserted therebetween, each jaw comprising a pair of opposing mandibles one longer than the other, each having teeth at one end and a trailing end remote therefrom and a seat defined in the backside thereof between said ends, and a shorter mandible having teeth at one end mating with said teeth of said opposing longer mandible, having a trailing end remote therefrom and terminating just beyond the distance of said seat in said backside of said longer mandible from said mating teeth to provide a very short moment arm at the trailing end of said shorter mandible for a force applied thereto compressing said trailing ends of said longer and shorter mandibles together, said shorter mandible having a pair of ears spaced close to the extremity of its trailing end and extending toward said longer mandible on either side thereof, and having a transverse axle between said ears to ride in said seat in said backside of said longer mandible, spring biasing means secured relative to said ears of said shorter mandible and disposed closely adjacent to said longer mandible opposite said seat to act upon said mandibles to bias the trailing ends thereof away from each other to close said teeth of said mandibles, and to hold said axle in said seat in said backside of said longer mandible, whereby said mandibles of each jaw are hinged to each other for relative rotation about said axle carried at a distance from the shorter one of said mandibles and seated in the backside of the longer one of said mandibles opposite said shorter mandible, and flexible fastener strips each having a plurality of interlocking means attached to the trailing ends of said longer mandibles of each of said jaws and arrangeable in releasable longitudinally adjustable mutually interlocking arrangement to limit the distance said jaws are allowed to move from each other.

7. The diaper cinch of claim 6 further characterized in that each of said interlocking means of said strips is a pliant strap, and one each of said interlocking straps includes a contact pad secured thereto and having an exposed fastening surface from which a multiplicity of yieldable hooks are directed outward and the other of said interlocking straps includes a contact pad secured thereto and having an exposed fastening surface from which a looped pile is directed outward, and said contact pads are positionable with said fastening surface in face-to-face relationship whereby said hooks are engageable in said pile.

8. The diaper cinch according to claim 6 further characterized in that each of said fastener strips includes a flexible strap with a velcro pad secured thereto and with an aperture in one end of said strap remote from the velcro pad thereon, and wherein at least one of said mandibles of each of said jaws has a flattened backside with an opening therein remote from the teeth thereof, whereby said strap passes through said opening and receives said teeth through said aperture and is drawn snugly against said mandible having said flattened backside by tensile force thereon.

9. The diaper cinch of claim 6 further characterized in that the teeth of each jaw include exposed overhanging teeth extending from one mandible and covered underbiting teeth extending from the other mandible thereof and the teeth of each of said mandibles are arranged at acute angles with respect to the length of said mandible, and the acute angle of the exposed overhanging teeth is less than the acute angle of said covered underbiting teeth.

10. The diaper cinch of claim 1 further characterized that the mandibles of each of said jaws are oriented at an acute angle relative to each other with the apex of said acute angle proximate to said teeth thereof.

11. A diaper cinch according to claim 6 further comprising a rod extending between said ears between said mandibles in each of said jaws and carried therefrom on the side of said longer mandible opposite said seat, and said spring biasing means comprises a coil spring positioned upon said rod with ends engaging said longer and shorter mandibles to bias said trailing ends thereof apart.

* * * * *